US010125062B2

United States Patent
Dang et al.

(10) Patent No.: US 10,125,062 B2
(45) Date of Patent: Nov. 13, 2018

(54) PROPYLENE PRODUCTION PROCESSES AND CATALYST SYSTEMS FOR USE THEREIN

(71) Applicant: Lyondell Chemical Technology, Houston, TX (US)

(72) Inventors: Vu Anh Dang, Bear, DE (US); Lei Zhang, League City, TX (US); Shaotian Wang, Downingtown, PA (US); Jude T. Ruszkay, Wilmington, DE (US); Edrick Morales, West Chester, PA (US); Steven T. Coleman, Humble, TX (US)

(73) Assignee: Lyondell Chemical Technology, L.P., Houston, TX (US)

(*) Notice: Subject to any disclaimer, the term of this patent is extended or adjusted under 35 U.S.C. 154(b) by 7 days.

(21) Appl. No.: 15/274,861

(22) Filed: Sep. 23, 2016

(65) Prior Publication Data

US 2017/0129831 A1    May 11, 2017

Related U.S. Application Data

(60) Provisional application No. 62/251,938, filed on Nov. 6, 2015.

(51) Int. Cl.
*C07C 6/04* (2006.01)
*C07C 5/25* (2006.01)

(52) U.S. Cl.
CPC ............ *C07C 6/04* (2013.01); *C07C 2521/04* (2013.01); *C07C 2521/08* (2013.01); *C07C 2521/10* (2013.01); *C07C 2523/28* (2013.01)

(58) Field of Classification Search
CPC .................................. C07C 6/04; C07C 5/25
USPC .................. 585/646, 664, 670, 324
See application file for complete search history.

(56) References Cited

U.S. PATENT DOCUMENTS

| | | | | |
|---|---|---|---|---|
| 3,285,982 | A * | 11/1966 | Nixon | B01J 27/16 502/208 |
| 7,220,886 | B2 * | 5/2007 | Podrebarac | C07C 6/04 585/324 |
| 2011/0021858 | A1 | 1/2011 | Ramachandran et al. | |
| 2012/0016172 | A1 | 1/2012 | Miyazoe et al. | |
| 2014/0179973 | A1 | 6/2014 | Debecker et al. | |
| 2016/0318830 | A1 * | 11/2016 | Stoyanova | C07C 6/04 |

FOREIGN PATENT DOCUMENTS

| | | |
|---|---|---|
| EP | 2415739 A1 | 2/2012 |
| FR | 2977890 A1 | 1/2013 |
| FR | 3007029 A1 | 12/2014 |
| WO | WO2015091905 A1 * | 6/2015 |

OTHER PUBLICATIONS

The International Search Report and Written Opinion for PCT/US2016/060451 dated Feb. 15, 2017.

* cited by examiner

*Primary Examiner* — Thuan D Dang

(57) ABSTRACT

Propylene production processes are discussed herein. The propylene production processes may include contacting an olefin feed including butene with ethylene in the presence of a catalyst system including a metathesis catalyst under reaction conditions sufficient to form a product stream including propylene, wherein the metathesis catalyst includes molybdenum and the reaction conditions include a reaction temperature of less than 250° C.

12 Claims, 3 Drawing Sheets

PROPYLENE PRODUCTION PROCESSES AND CATALYST SYSTEMS FOR USE THEREIN

CROSS-REFERENCE TO RELATED APPLICATIONS

This application claims the benefit of priority to U.S. Provisional Application No. 62/251,938, filed on Nov. 6, 2015, which is incorporated herein by reference in its entirety.

FIELD OF THE INVENTION

The present technology generally relates to catalyzed metathesis processes.

BACKGROUND OF THE INVENTION

This section introduces information that may be related to or provide context for some aspects of the techniques described herein and/or claimed below. This information should be regarded as a background for facilitating a better understanding of that which is disclosed herein.

Metathesis reactions to produce propylene may include feeding a metathesis feed stream including butene, which may include mixtures of 1-butene and 2-butene, to a metathesis reactor loaded with a mixture of metathesis catalyst and an isomerization catalyst. Such processes provide for efficiencies by utilizing a single process for the production of propylene from available feedstocks. However, such reactions may have high reaction temperature requirements (e.g., temperatures greater than 300° C.) for achieving acceptable propylene production rates. Unfortunately, such high temperatures can lead to shorter catalyst life, increased production costs and lowered product yield, for example.

The present technology is directed to resolving, or at least reducing, the problems mentioned above.

SUMMARY OF THE INVENTION

Various embodiments of the present technology include propylene production processes. The propylene production processes may include contacting an olefin feed, including butene with ethylene, in the presence of a catalyst system including a metathesis catalyst under reaction conditions sufficient to form a product stream including propylene, wherein the metathesis catalyst includes molybdenum, and the reaction conditions include a reaction temperature of less than 250° C.

One or more embodiments include the process of the preceding paragraph, wherein the catalyst system further includes a support material including an inorganic oxide.

One or more embodiments include the process of any preceding paragraph, wherein the process exhibits a propylene selectivity of at least 85 wt. %.

One or more embodiments include the process of any preceding paragraph, wherein the catalyst system further includes an isomerization catalyst.

One or more embodiments include the process of any preceding paragraph, wherein the catalyst system includes a weight ratio of isomerization catalyst to metathesis catalyst in a range of 5:1 to 1:5.

One or more embodiments include the process of any preceding paragraph, wherein the catalyst system includes a greater concentration of metathesis catalyst than isomerization catalyst.

One or more embodiments include the process of any preceding paragraph, wherein the olefin feed contacts the isomerization catalyst prior to contacting the metathesis catalyst.

One or more embodiments include the process of any preceding paragraph, wherein the olefin feed contacts the metathesis catalyst prior to contacting the isomerization catalyst.

One or more embodiments include the process of any preceding paragraph, wherein the olefin feed contacts the isomerization catalyst essentially simultaneously with the metathesis catalyst.

One or more embodiments include the process of any preceding paragraph, wherein the isomerization catalyst includes magnesium oxide or potassium carbonate.

One or more embodiments include the process of any preceding paragraph, wherein the isomerization catalyst includes magnesium oxide and further includes a binder selected from alumina, silica, clays, inorganic oxides and combinations thereof.

One or more embodiments include the process of any preceding paragraph, wherein the isomerization catalyst includes at least 50 wt. % magnesium oxide and from 10 wt. % to 40 wt. % binder.

One or more embodiments include the process of any preceding paragraph, wherein the binder exhibits an alpha crystalline structure.

One or more embodiments include the process of any preceding paragraph, wherein the reaction temperature is in a range of 110° C. to 200° C.

One or more embodiments include the process of any preceding paragraph, further including independently activating the metathesis catalyst and the isomerization catalyst prior to contact with the olefin feed.

One or more embodiments include the process of any preceding paragraph, further including activating the metathesis catalyst, the isomerization catalyst or a combination thereof prior to contact with the olefin feed, wherein the activating includes contact with an inert gas at an activation temperature in a range of 300° C. to 600° C.

One or more embodiments include the process of the preceding paragraph, wherein the activation temperature is in a range of 450° C. to 600° C.

One or more embodiments include the process of any preceding paragraph, wherein the catalyst system lacks an isomerization catalyst.

One or more embodiments include the process of any preceding paragraph, wherein the olefin feed includes at least 90 wt. % 2-butene, based on the total percentage of butenes in the olefin feed.

One or more embodiments include the process of any preceding paragraph, wherein the product stream includes at least 45 wt. % propylene.

One or more embodiments include the process of any preceding paragraph, wherein the catalyst system exhibits a stability of at least 24 hours.

The above paragraphs present a simplified summary of the presently disclosed subject matter in order to provide a basic understanding of some aspects thereof. The summary is not an exhaustive overview. Its sole purpose is to present some concepts of the present technology as a prelude to the more detailed description set forth below.

BRIEF DESCRIPTION OF THE DRAWINGS

Certain embodiments of the claimed subject matter may be better understood by the following description taken in conjunction with the accompanying drawings, in which like reference numerals identify like elements, and in which:

DETAILED DESCRIPTION OF THE INVENTION

Figure 1:
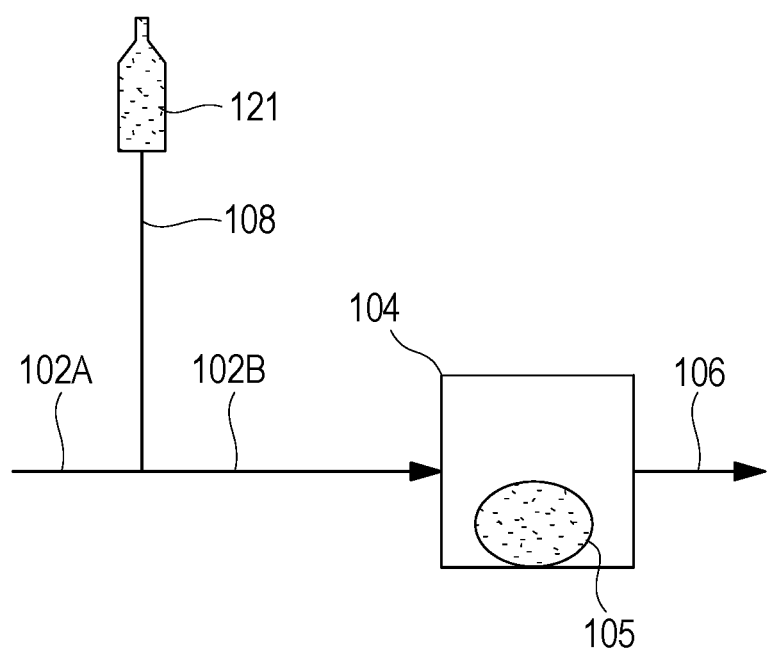
FIG. 1 illustrates a propylene production process in accordance with certain embodiments of the present technology.

Illustrative embodiments of the subject matter claimed below will now be disclosed. In the interest of clarity, not all features of an actual implementation are described in this specification. It will be appreciated that in the development of any such actual embodiment, numerous implementation-specific decisions should be made to achieve the developers' specific goals, such as compliance with system-related and business-related constraints, which will vary from one implementation to another. Moreover, it will be appreciated that such a development effort would be a routine undertaking for those of ordinary skill in the art having the benefit of this disclosure.

The embodiments disclosed herein may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein may refer to a value within a specified range and encompasses every value within the specified range.

Embodiments described herein may include olefin production processes. The olefin production processes include contacting one or more olefin feed(s) in the presence of a metathesis catalyst under reaction conditions sufficient to form the desired olefin product. It will be appreciated, however, that the resulting reaction product can be produced directly from a reaction between the added reagents or from an intermediate from one or more of the added reagents produced in the reaction mixture. The term "olefin" refers to a hydrocarbon compound containing at least one carbon-carbon double bond. As used herein, the term "olefin" may further encompass hydrocarbons having more than one carbon-carbon double bond (e.g., di-olefins, tri-olefins, etc.). In some embodiments, the term "olefin" refers to a group of carbon-carbon double bond-containing compounds with different chain lengths. In some embodiments, the term "olefin" refers to polyolefins, straight, branched and/or cyclic olefins, for example. Specific examples of olefins include, but are not limited to, ethylene, propylene, 1-butene, 2-butene, methylpropylene, 1-pentene, 2-pentene, 1-hexene, 2-hexene, 3-hexene, 1-heptene, 2-heptene, 3-heptene, 1-octene, 2-octene, 3-octene, 4-octene, and the like.

The source of the olefin feed may be any hydrocarbon stream including the targeted olefin. For example, the source may be a mixed olefin stream. The mixed olefin stream may be a petrochemical and/or refinery process stream, for example. A variety of streams from chemical processes (including petrochemical and/or refinery processes) may be incorporated for supplying the internal (or alternatively, alpha) olefin utilized for the isomerization processes herein. Such chemical processes may include separation processes prior to the subsequent use of the streams. For example, the effluent from a given process, such as steam cracking, may be separated via fractionation into a variety of cuts based on their boiling point prior to sending such cuts for further processing or use. The term "cut" refers to that portion of crude oil that boils within certain temperature limits, such as limits based on a crude assay "true boiling point" basis. Accordingly, it is contemplated that chemical product streams may be processed by any method capable of producing a stream for use in the processes herein, e.g., as the olefin feed, including, but not limited to, fractionation and/or hydrogenation.

In one or more embodiments, the olefin feed includes at least 40 wt. %, or at least 45 wt. %, or at least 50 wt. %, or at least 55 wt. %, or at least 60 wt. %, or at least 70 wt. %, or at least 75 wt. %, or at least 80 wt. %, or at least 90 wt. % or at least 95 wt. % internal olefin. As used herein, the term "internal olefin" refers to an olefin having an internal double bond as opposed to olefins having double bonds at the alpha position. For example, the olefin feed may include at least 80 wt. % 2-butene.

In one or more specific embodiments, the olefin feed includes butene and, as such, the olefin product includes propylene. However, while the embodiments below may be described below particularly with reference to the conversion of butene to form propylene, the conversion of pentene, hexene, heptene and the like are encompassed herein.

In one or more embodiments, the molar ratio of ethylene to butene contacting the metathesis catalyst may be in a range of 0.1:1 to 3.0:1, or 2:1 to 1:1, or 1.1:1 to 1.2:1, or 0.8:1 to 2:1 or 1.5:1 to 2:1, for example. The ethylene may be fed to the reaction by methods available in the relevant art. For example, the ethylene may be fed to the reaction separate from the olefin feed. Alternatively, the ethylene may be combined with the olefin feed prior to introduction to the reaction. However, regardless of what method is utilized to introduce the ethylene to the reaction, the amount and/or concentration of butene (e.g., 2-butene or 1-butene) in the olefin feed refers to that prior to contact with ethylene.

In the embodiments described herein, the metathesis catalyst includes molybdenum. For example, the metathesis catalyst may include molybdenum oxide ($MoO_3$). In one or more embodiments, the olefin production process includes contacting the olefin feed with an isomerization catalyst as well as the metathesis catalyst. Such contact can occur simultaneously or sequentially. For example, the metathesis catalyst and the isomerization catalyst may be combined prior to contacting the olefin feed. Alternatively, the olefin feed may contact the isomerization catalyst prior to contacting the metathesis catalyst. Alternatively, the olefin feed may contact the metathesis catalyst prior to contacting the isomerization catalyst. Such sequential contact can occur by disposing each catalyst within sequentially arranged catalyst beds, for example. Such beds can be disposed within the same reaction vessel or separate reaction vessels, for example. It is contemplated that in such a sequential arrangement, the ethylene may be introduced to the reaction either upstream or downstream of the isomerization catalyst.

As used herein, the terms "up" and "down", "upper" and "lower", "upwardly" and "downwardly", "upstream" and "downstream", "above" and "below" and other like terms indicating relative positions above or below a given point or element are used in this description to describe some embodiments of the technology.

The isomerization catalyst may be adapted to convert excess 1-butene present a point of equilibrium in the olefin feed to 2-butene for subsequent reaction to propylene. Isomerization catalysts may include zeolites, acidic zeolites, acidic clays, metal oxides, mixed metal oxides and combinations thereof, for example, as described in U.S. Pat. Nos. 5,153,165 and 4,992,613, and U.S. Pat. App. Pub. Nos. 2004/0249229 and 2006/0084831, which are incorporated herein by reference in their entirety.

In one or more embodiments, the isomerization catalyst includes at least one element from Group IA or Group IIA of the Periodic Table of the Elements. For example, the isomerization catalyst may include an alkali metal compound or salt. Representative, non-limiting embodiments of alkali metal compounds or salts for use in the isomerization catalyst include lithium nitrate, sodium nitrate, potassium nitrate, cesium nitrate, lithium carbonate, sodium carbonate, potassium carbonate, cesium carbonate, lithium oxalate, sodium oxalate, potassium oxalate, lithium hydroxide, sodium hydroxide, potassium hydroxide, lithium chloride, lithium iodide, lithium bromide, sodium chloride, sodium iodide, potassium chloride, potassium iodide, calcium oxide, magnesium oxide, strontium oxide, barium oxide, lithium oxide and combinations thereof.

In one or more embodiments, the isomerization catalyst includes a basic double-bond isomerization catalyst, such as a metal oxide. The metal of the metal oxide may include an alkali or alkaline earth or Group 3 metal. For example, the metal oxide may be selected from magnesium oxide, calcium oxide, barium oxide, lithium oxide, potassium oxide, potassium carbonate, tungsten oxide and combinations thereof. In one or more specific embodiments, the metal oxide is magnesium oxide, potassium oxide, potassium carbonate or combinations thereof.

The isomerization catalyst may further include a binder. Typical binder materials may include talc, inorganic oxides, clays and clay minerals, ion-exchanged layered compounds, diatomaceous earth compounds, zeolites or combinations thereof, for example. Specific inorganic oxides include silica, alumina, magnesia, titania and zirconia, for example. In one or more embodiments, the binder may have a gamma structure (i.e., a rhombohedral crystal structure) or an alpha structure (i.e., a cubic crystal structure).

In one or more specific embodiments, the binder is selected from silica, alumina and combinations thereof. The inorganic oxides may have an average particle size (as measured by ASTM-1921) in a range of 5 microns to 600 microns or 10 microns to 100 microns, a surface area (as measured by ASTM-D1993) in a range of 10 m$^2$/g to 1,000 m$^2$/g or 10 m$^2$/g to 100 m$^2$/g and a pore volume (as measured by ASTM-D4284) in a range of 0.1 cc/g to 3.5 cc/g or 0.1 cc/g to 1.0 cc/g, for example.

In one or more specific embodiments, the binder has an alpha crystalline structure. It is contemplated that the binder may be modified so as to have an alpha crystalline structure at the time of contact with the isomerization feed stream (e.g., the binder may be modified before or after contact with the metal oxide but prior to contact with the isomerization feed stream). Such modification may include calcining a binder having a gamma crystalline structure for a time sufficient to modify the crystalline structure of the binder to the alpha structure. The calcining may include contacting the binder, the isomerization catalyst or combinations thereof with a gas. Gases for use with the present technology may include inert or oxidizing gases, such as helium, nitrogen, argon, neon, oxygen, air, carbon dioxide and combinations thereof, for example. Calcining may occur at a calcining temperature in a range of 450° C. to 1200° C., or 600° C. to 1100° C., or 650° C. to 1000° C., for example. The time of calcining will vary by process, but may occur for a time in a range of 1 hour to 10 hours, including 2 hours to 6 hours.

When utilizing a binder, the isomerization catalyst may be formed by contacting the metal oxide with the binder for a time sufficient to incorporate the metal oxide into the binder in accordance with contact methods available in the relevant art. Such contact methods may include temperatures in a range of room temperature, e.g. about 20° C., to 350° C., or 50° C. to 250° C., or 100° C. to 200° C., and mixing times in a range of 2 minutes (min) to 30 min, for example. As used herein, "room temperature" means that a temperature difference of a few degrees does not matter to the phenomenon under investigation, such as a preparation method. In some environments, room temperature may include a temperature in a range of about 20° C. to about 28° C., while in other environments, room temperature may include a temperature in a range of about 10° C. to about 32° C., for example. However, room temperature measurements may not include close monitoring of the temperature of the process and therefore such a recitation does not intend to bind the embodiments described herein to any predetermined temperature range.

The isomerization catalyst may include binder in a range of 5 wt. % to 50 wt. %, or 10 wt. % to 40 wt. %, or 15 wt. % to 30 wt. %, and metal oxide in a range of at least 1 wt. %, or at least 5 wt. %, or at least 30 wt. % or at least 90 wt. %.

The metal oxide may be pre-treated prior to contact with the binder. For example, the metal oxide may be treated in a dry inert gas to remove residual water and carbon dioxide. The inert gas may include any gas which is non-reactive under the conditions employed. Illustrative, non-limiting examples of inert gases include argon and nitrogen. Furthermore, the metal oxide may be a "high purity" metal oxide. As used herein, the term "high purity" refers to a metal oxide having an impurity level of less than 500 ppm of transition metals and less than 2000 ppm of sulfur and/or phosphorous.

The weight ratio of isomerization catalyst to metathesis catalyst in the catalyst system can vary widely. For example, the weight ratio can vary in an amount in a range of 0:1 (i.e., no isomerization catalyst) to 100:1, or 0.5:1 to 80:1, or 0.1:1 to 20:1, or 0.1:1 to 10.5:1, or 0.5:1 to 0.25:1. In one or more embodiments, the catalyst system includes more metathesis catalyst than isomerization catalyst. For example, the catalyst system may include at least 50%, or at least 70%, or at least 75%, or at least 80%, or at least 100%, or at least 150%, or at least 175%, or at least 400% more metathesis catalyst than isomerization catalyst. Various embodiments described herein are capable of forming propylene at high selectivity/productivity without the use of the isomerization catalyst. In fact, some embodiments include reaction of the olefin feed and the ethylene in the absence of an isomerization catalyst.

The components of the catalyst system may or may not be associated with or bound to a support, either in combination with each other or separate from one another. For example, each catalyst component (e.g., the isomerization catalyst and the metathesis catalyst) may reside on a single support material such that the catalyst system is a supported catalyst system. However, it is also contemplated that the catalysts may be independently supported (i.e., each material is supported on a separate, distinct, support material). In such embodiments, the separate support materials may include the same or different compounds. It is further contemplated that one catalyst may be supported while the other is not.

Illustrative, non-limiting examples of support materials include inorganic oxides (e.g., silica, alumina, magnesia, titania and zirconia), zeolites, clays and mixtures thereof, for example. Supporting methods include those available in the relevant art such as adsorption, ion-exchange, impregnation and sublimation. When supported, the catalyst system may include a metathesis catalyst in a range of 1 wt. % to 30 wt. % or 5 wt. % to 20 wt. %, or 5 wt. % to 50 wt. %, or 10 wt. % to 40 wt. %, or 15 wt. % to 30 wt. %, or at least 50 wt. %, or at least 75 wt. %, for example. When supported, the catalyst system may include isomerization catalyst in a range of 1 wt. % to 30 wt. % or 5 wt. % to 20 wt. %, or 5 wt. % to 50 wt. %, or 10 wt. % to 40 wt. %, or 15 wt. % to 30 wt. %, or at least 50 wt. %, or at least 75 wt. %.

It is further contemplated that one or more components of the metathesis catalyst, the isomerization catalyst or combinations thereof may be activated. For example, the activation may include contact with an inert gas, at a temperature of less than 600° C., or in a range of 300° C. to 700° C., or 400° C. to 600° C., or 300° C. to 600° C., or 450° C. to 600° C. for a time sufficient to activate the catalyst. For example, the time may be in a range of 2 hours to 48 hours, or 4 hours to 40 hours or at least 6 hours, for example. The inert gas may include any inert gas described herein.

While it is contemplated that when both the isomerization and metathesis catalyst are activated, such activation may occur simultaneously or sequentially, within the same or different vessels, one or more embodiments include activating the isomerization and metathesis catalysts independent of one another. In doing so, it has been observed that catalyst contact with by-products formed in activation of the other catalyst can be avoided, thus improving the subsequent catalyst activity. For example, each catalyst can be activated in a vessel having its own vent stream so that any formed by-products are directly vented without contacting the other catalyst. It is contemplated that the activation conditions, such as temperature and pressure, for each catalyst may be the same or different. Unexpectedly, it has been observed that independently activating the isomerization and metathesis catalysts can result in increased catalyst stability. It is recognized that the terms "increasing" and "decreasing" are relative terms. In one or more embodiments, the catalyst stability can be increased from just a few hours to several days. For example, the catalyst system may exhibit stability for a time in a range of from 24 hours to 80 hours, or from 34 hours to 70 hours, or from 40 hours to 65 hours. As used herein, the term "catalyst stability" refers to a process wherein the yield of targeted product does not decrease more than 10%.

Typical olefin production processes occur at reaction temperatures of at least 250° C. For example, reaction temperatures may include values in a range of from 300° C. to 600° C. High temperatures favor the isomerization of the internal olefin to the alpha olefin. However, high temperatures can cause catalyst coking, thereby shortening catalyst life. Further, it has been observed that at higher temperatures, i.e., at least about 400° C., unacceptable levels of adventitious by-products, such as isobutene, can be formed. However, the embodiments described herein are capable of operation at reaction temperatures of less than 250° C. For example, the embodiments described herein may utilize reaction temperatures of less than 250° C., or in a range of 100° C. to 200° C., or 120° C. to 200° C. Even at such low reaction temperatures, sufficient selectivity and productivity can be obtained with the embodiments described herein. The term "selectivity" refers to the weight percentage of input/reactant converted to a desired output/product. In one or more embodiments, the propylene selectivity is at least 85 wt. %, or at least 90 wt. %, or at least 92 wt. %, or at least 95 wt. %, for example. The term "productivity" refers to the weight of product produced per weight of the catalyst used in a process per hour of reaction at a standard set of conditions (e.g., grams product/gram catalyst/hr). In one or more embodiments, the productivity (which may also be used interchangeably with the term "yield") is at least 40%, or at least 45%, or at least 50%.

The reaction conditions further may include a pressure in a range of 20 kilopascals (kPa) to 3800 kPa, or 20 kPa to 3500 kPa, or 35 kPa to 3000 kPa, for example. The reaction may occur at a WHSV in a range of 0.01 $hr^{-1}$ to 1000 $hr^{-1}$, or 0.1 $hr^{-1}$ to 200 $hr^{-1}$, or 0.1 $hr^{-1}$ to 50 $hr^{-1}$ or 0.1 $hr^{-1}$ to 40 $hr^{-1}$.

The contact time utilized to obtain a commercially sufficient yield of olefin product depends upon several factors, such as the activity of the catalyst, temperature and pressure, for example. However, in some embodiments, the length of time during which the olefin feed and the ethylene are contacted with the metathesis catalyst can vary for a time in a range of 0.1 seconds (s) to 4 hours or 0.5 s to 0.5 hours, for example. The reaction may be conducted batch-wise or continuously with fixed catalyst beds, slurried catalyst, fluidized beds, or by using any other conventional contacting techniques.

Further processing of the olefin product, such as separation, is contemplated and within the scope of the technology. Such processes are available in the relevant art and therefore are not described in detail herein.

Referring now to FIG. 1, a simplified process flow diagram of a process for producing propylene according to embodiments disclosed herein is illustrated. FIG. 1 illustrates a process including introducing a metathesis feed stream 102B to a metathesis reactor 104 having a catalyst system 105 disposed therein to form metathesis product stream 106. FIG. 1 illustrates a specific embodiment wherein ethylene 121 is mixed with the metathesis feed stream 102A via line 108 to form metathesis feed stream 102B.

EXAMPLES

To facilitate a better understanding of the present technology, the following examples of embodiments are given. In no way should the following examples be read to limit the scope of the technology.

Example 1

A variety of catalyst samples were utilized within a metathesis reaction to evaluate the effectiveness of such samples. Sample A1 was an inventive $MoO_3$ compound on an alumina metathesis catalyst. Comparative Sample B1 was a $WO_3$ compound on a silica metathesis catalyst.

The catalyst samples were utilized in a metathesis reaction. The metathesis reaction included feeding butene-2 and ethylene to a bench scale reactor having a metathesis catalyst disposed therein at various reaction temperatures. Analysis of the resultant product was then undertaken via on-line gas chromatography (GC). The results are shown in TABLE 1 below.

TABLE 1

| Catalyst Sample | Propylene Yield (wt. %) | $C^{5+}$ (wt. %) | Reaction T (° C.) |
|---|---|---|---|
| A1 | 52.7 | 2.1 | 200 |
| B1 | 0 | 0 | 200 |
| B1 | 49.9 | 1.4 | 425 |
| A1 | 46.5 | 1.1 | 175 |
| B1 | 0 | 0 | 175 |
| B1 | 16.8 | 0.2 | 350 |

It was observed that Comparative Sample B1 produces no detectable propylene levels at low (i.e., 200° C. or less) temperatures.

Example 2

A variety of catalyst samples were utilized within a metathesis reaction to evaluate the effectiveness of such samples. Sample A2 was a mixed isomerization (MgO)/metathesis ($MoO_3$ on alumina) catalyst. Comparative Sample B2 was a mixed isomerization (MgO)/metathesis ($WO_3$ on silica) catalyst.

The catalyst samples were utilized in a metathesis reaction. The metathesis reaction included feeding butene-2 and ethylene to a bench scale reactor having the catalyst disposed therein at various isomerization:metathesis catalyst ratios. Analysis of the product was then undertaken via on-line gas chromatography (GC). The results are shown in Table 2 below.

TABLE 2

| Catalyst Sample | Molar Ratio of isomerization:metathesis catalyst | Propylene Yield (wt. %) | Propylene selectivity (wt. %) | Butene Conversion (wt. %) | Reaction T (° C.) |
|---|---|---|---|---|---|
| A2 | 3:1 | 22.7 | 81.1 | 30.6 | 200 |
| A2 | 2:2 | 44.3 | 87.6 | 50.7 | 200 |
| A2 | 1:3 | 52.2 | 92.3 | 55 | 200 |
| B2 | 3:1 | 5.1 | 32.4 | 4.4 | 200 |
| B2 | 3:1 | 48.5 | 88.8 | 56.2 | 350 |

It was surprisingly observed that by increasing the molar ratio of the metathesis:isomerization catalyst, increased propylene yield and selectivity were achieved.

Figure 2:
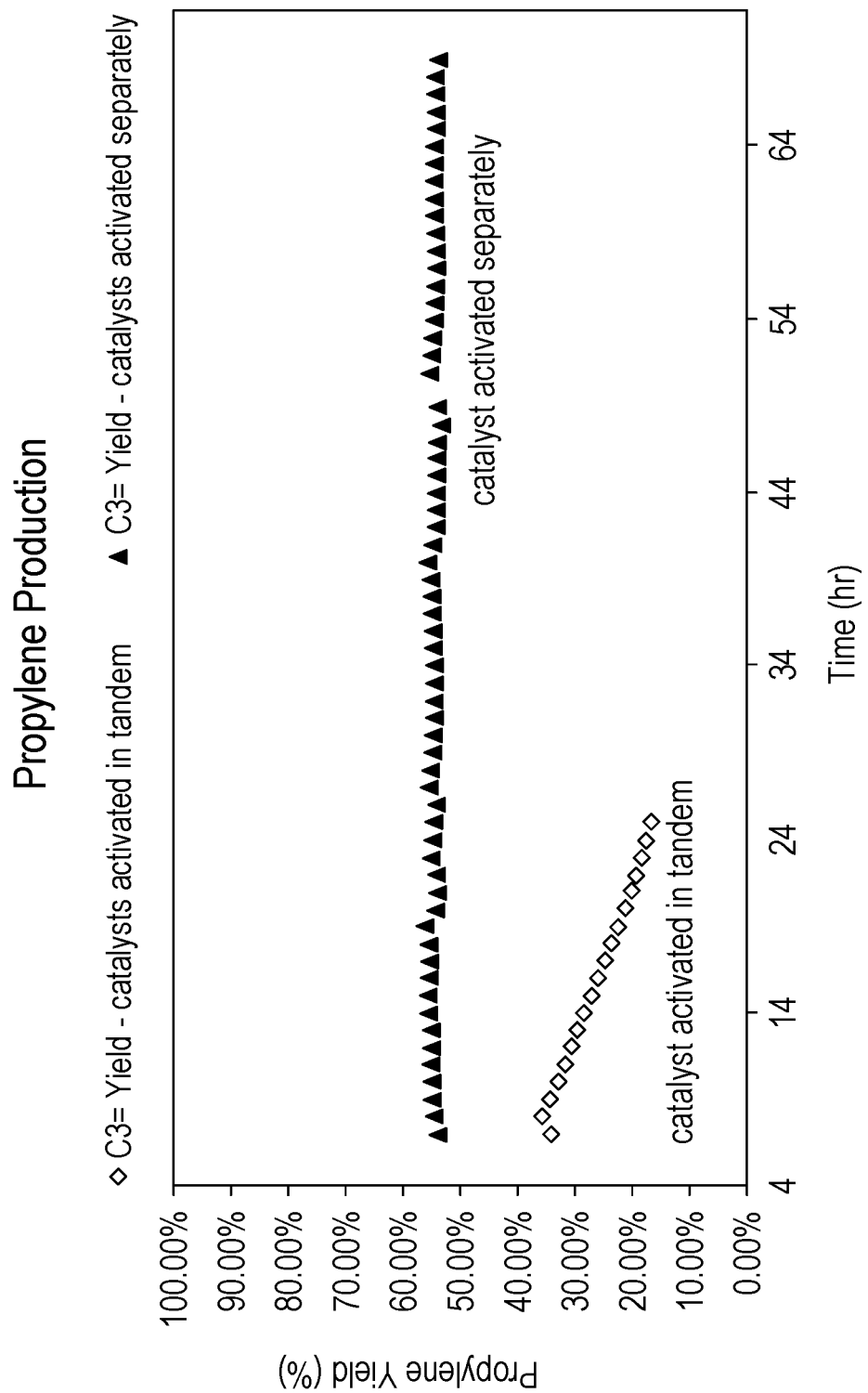
FIG. 2 illustrates a plot of propylene production conditions over time for various catalyst activation conditions in accordance with certain embodiments of the present technology.
Figure 3:
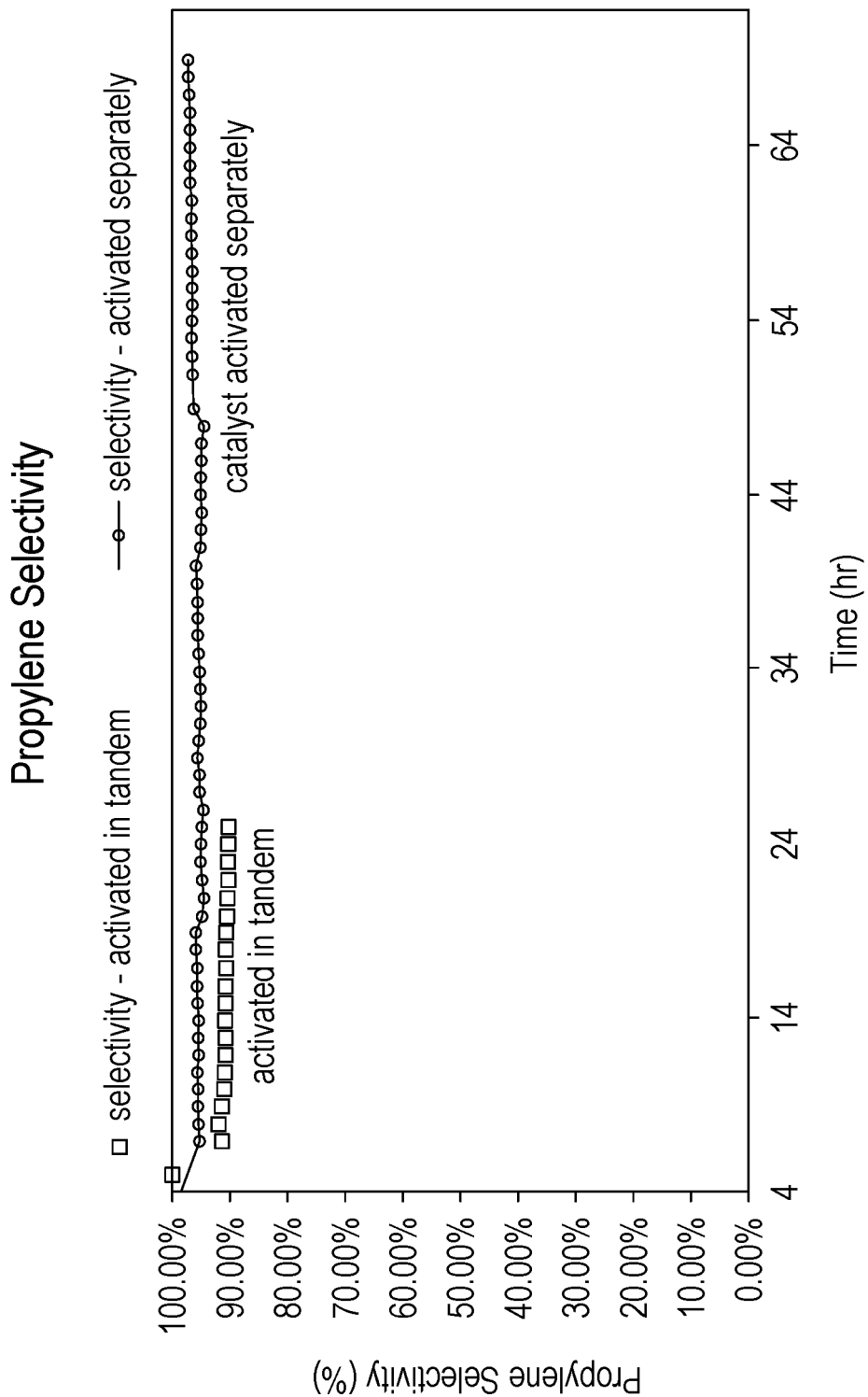
FIG. 3 illustrates a plot of propylene selectivity over time for various catalyst activation conditions in accordance with certain embodiments of the present technology.

Example 3: A study evaluating the effectiveness of the activation of a mixed catalyst system (isomerization-potassium carbonate on alumina/metathesis-molybdenum trioxide on alumina) was undertaken. In the first run, the mixed catalyst system included placing both the isomerization and metathesis catalyst in one reactor. The catalysts were then simultaneously activated by treating both catalysts at 570° C. under a constant flow of argon gas. When the subsequent reaction was run at 120° C. with butene and ethylene fed into the reactor, the reaction was short-lived (e.g., the propylene yield was high at the beginning but then dramatically decreased after a few hours of run time). Similarly, a poor performance was also observed in a reaction in which the isomerization and metathesis catalysts were placed in two separate reactors and then were activated in-tandem. Activating the catalysts in-tandem included flowing argon through the first reactor and then to the second reactor at activation temperatures of 570° C. A third study was undertaken where isomerization and metathesis catalysts were activated at 570° C. in two separate reactors which were equipped with separate argon lines and vent lines. It was observed that activating the catalysts separately instead of in-tandem prolonged the catalyst life from just a few hours to several days (see, FIG. 2). It also improved the catalyst selectivity from 93% to 95% (see, FIG. 3) and increased propylene production from less than 40% to 55% (see, FIG. 2).

What is claimed is:

1. A process comprising:
   contacting an olefin feed comprising butene with ethylene in the presence of a mixed catalyst system comprising a metathesis catalyst and an isomerization catalyst under reaction conditions sufficient to form a product stream comprising propylene, wherein the metathesis catalyst comprises molybdenum and the reaction conditions comprise a reaction temperature of less than 250° C. and the isomerization catalyst comprises at least 50wt. % magnesium oxide and 10-40 wt. % alumina binder.

2. The process of claim 1, wherein the process exhibits a propylene selectivity of at least 85 wt. %.

3. The process of claim 1, wherein the catalyst system comprises a weight ratio of isomerization catalyst to metathesis catalyst in a range of 5:1 to 1:5.

4. The process of claim 1, wherein the catalyst system comprises a greater concentration of metathesis catalyst than isomerization catalyst.

5. The process of claim 1, wherein the olefin feed contacts the isomerization catalyst simultaneously with the metathesis catalyst.

6. The process of claim 1, wherein the binder exhibits an alpha crystalline structure.

7. The process of claim 1, wherein the reaction temperature is in a range of 100° C. to 200° C.

8. The process of claim 1, further comprising independently activating the metathesis catalyst and the isomerization catalyst prior to contact with the olefin feed.

9. The process of claim 1, further comprising activating the metathesis catalyst, the isomerization catalyst or a combination thereof prior to contact with the olefin feed, wherein the activating comprises contact with an inert gas at an activation temperature of from 300° C. to 600° C.

10. The process of claim 1, wherein the olefin feed comprises at least 90 wt .% 2-butene based on the total percentage of butanes in the olefin feed.

11. The process of claim 1, wherein the product stream comprises at least 45 wt. % propylene.

12. The process of claim 8, wherein the catalyst system is stable for a period of at least 24 hours.

* * * * *

UNITED STATES PATENT AND TRADEMARK OFFICE
CERTIFICATE OF CORRECTION

| | |
|---|---|
| PATENT NO. | : 10,125,062 B2 |
| APPLICATION NO. | : 15/274861 |
| DATED | : November 13, 2018 |
| INVENTOR(S) | : Dang et al. |

Page 1 of 1

It is certified that error appears in the above-identified patent and that said Letters Patent is hereby corrected as shown below:

In the Specification

In Column 3, Line 24, delete "he" and insert -- be --
In Column 6, Line 41, delete "Furtheiwore," and insert -- Furthermore, --
In Column 7, Line 1, delete "he" and insert -- be --

In the Claims

In Column 10, Claim 6, Line 38, before "binder" insert -- alumina --

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*